United States Patent [19]

Deselaers et al.

[11] 4,080,393

[45] Mar. 21, 1978

[54] METHOD OF RECTIFYING SOLVENTS OF THE CHLORINATED HYDROCARBON SERIES

[75] Inventors: Kurt Deselaers; Rudolf Stephan, both of Troisdorf-Sieglar, Germany

[73] Assignee: Dynamit Nobel Aktiengesellschaft, Troisdorf, Germany

[21] Appl. No.: 728,696

[22] Filed: Oct. 1, 1976

[30] Foreign Application Priority Data

Oct. 2, 1975 Germany .............................. 2543992

[51] Int. Cl.$^2$ ............................................ C07C 25/02
[52] U.S. Cl. .............................. 260/652 P; 260/654 S
[58] Field of Search ..................... 260/652 P, 654 S

[56] References Cited

U.S. PATENT DOCUMENTS 3,647,895   3/1972   Fruhwirth et al. .............. 260/652 P

FOREIGN PATENT DOCUMENTS 37-15607   1/1962   Japan ............................. 260/654 S
773,632   5/1957   United Kingdom.

*Primary Examiner*—C. Davis
*Attorney, Agent, or Firm*—Burgess, Dinklage & Sprung

[57] ABSTRACT

A method for rectifying chlorinated hydrocarbon to removed therefrom substances which discolor or tarnish metals by contacting the chlorinated hydrocarbon with a compound which is an alkanolamine, morpholine, an N $C_{1-8}$ alkyl morpholine, hexamethyleneimine or a mixture thereof and thereafter water washing the so contacted chlorinated hydrocarbon.

12 Claims, No Drawings

METHOD OF RECTIFYING SOLVENTS OF THE CHLORINATED HYDROCARBON SERIES

BACKGROUND OF THE INVENTION

1. Field of the Invention

The present invention relates to the rectification of solvents of the chlorinated hydrocarbon series to enable them to be used for the treatment of noble metals, such as copper or silver, without causing discoloration of the surface of these metals.

2. Discussion of the Prior Art

Chlorinated hydrocarbons such as trichlorethylene and perchlorethylene are used for the cleaning, degreasing or drying of metal objects. This treatment can be performed with the said solvents either in the liquid phase or in the vaporous phase. For the practical use of the chlorinated hydrocarbons they must be stabilized to protect them against degradation or prevent them from attaching the articles being treated. Such degradation is caused, for example, by the oxidizing action of atmospheric oxygen on the double bond of perchlorethylene or trichlorethylene, as the case may be. The hydrogen chloride that is thus released attacks the metal surfaces. To forestall this phenomenon, the solvents must, after rectification by distillation, be carefully neutralized, dried, and then stabilized. Phenols, amines, dioxane, nitro compounds, esters, nitriles and epoxides, for example, have been described as stabilizers.

Depending on the method by which they have been produced, in some cases a special treatment of the chlorinated hydrocarbons is necessary prior to their stabilization. For example, in German "Offenlegungsschrift" No. 2,111,735 a description is given of the preliminary treatment of chlorinated hydrocarbons with diamines for the purpose of removing oxidizing compounds which otherwise would call for an excessively great consumption of stabilizer. This treatment with diamines is especially necessary when the chlorinated hydrocarbons have been produced by an oxychlorination process and contain oxygenous compounds of the type Cl—R—O—OR—Cl or

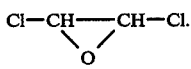

With or without this treatment, it is possible sufficiently to stabilize chlorinated hydrocarbons, especially unsaturated chlorinated hydrocarbons. The use of the substances named above generally suffices to protect these solvents and thus also the metal surfaces being treated.

If, however, objects made of valuable metals, such as silver or copper, in which the external appearance of the metal surface after hot or cold treatment with the solvents is important, are treated with the above-named already stabilized solvents and cleaning agents, the mere addition of the stabilizers described in the literature is often insufficient. Thus it is often observed that copper surfaces are darkened and silver surfaces acquire a yellowish discoloration when they are subjected to treatment with hot chlorinated hydrocarbons, for the purpose of drying them, for example. Particularly in the case of metal surfaces of decorative value, this effect is most undesirable.

The surface discoloration effect occurs especially when a chlorinated hydrocarbon is involved which has been produced from a variety of prechlorinated products of different composition. These chlorinated hydrocarbon mixtures originate in chemical plants in which vinyl chloride is produced in a series of steps from ethylene, chlorine and hydrogen chloride by chlorination, oxychlorination and dehydrochlorination. In this process a plurality of more or less chlorinated and partially also oxychlorinated hydrocarbons are formed as by-products which must be separated, by distillation for example, and destroyed. However, they can also be used alone or together with 1,2-dichlorethane in a catalytic high-temperature chlorination for the production of perchlorethylene and/or trichlorethylene. As a result of the multiplicity of the components which in this case react with chlorine, compounds are also formed in small amounts which, when the solvents are used on copper or silver, produce the tarnishing action described above. This undesirable effect is not prevented by the sole addition of the conventional stabilizers.

One method of preventing the "tarnishing" of copper objects upon treatment with chlorinated hydrocarbons is described in German "Offenlegungsschrift" No. 2,036,939, in which the presence of sulfur compounds in the chlorinated hydrocarbons is given as the cause. The elimination of these undesirable sulfur compounds is accomplished in accordance with the method described in that specification by the addition of phenol, cresol or xylenol. The sulfur compounds in chlorinated hydrocarbons are not, however, the only cause of the above-named tarnishing of the noble metals. Even if sulfur-free chlorinated hydrocarbons such as those obtained by the vinyl chloride production processes described above are treated with phenols, the discoloration of the metal surfaces is not prevented.

SUMMARY OF THE INVENTION

In accordance with this invention it has been surprisingly found that the discoloration of copper and/or silver surfaces when treated with a chlorinated hydrocarbon can be prevented if the chlorinated hydrocarbon is treated in accordance with the invention which comprises contacting the chlorinated hydrocarbon with a compound which is an alkanolamine, morpholine, an N-C$_{1-8}$ alkyl morpholine, hexamethyleneimine, N-C$_{1-8}$ alkyl hexamethyleneimine or a mixture thereof and thereafter water washing the so contacted chlorinated hydrocarbon.

The claimed compounds are best dissolved in water, so that the treatment of the chlorinated hydrocarbons, which are very difficultly soluble in the aqueous solution of these compounds, will technically be a liquid-to-liquid extraction. It is important that the compounds thus used be then removed again by a water washing; they are not, therefore, used as stabilizers of the chlorinated hydrocarbon.

The water washing removes not only the nitrogenous compounds used in the treatment of the chlorinated hydrocarbons, but also the product of their reaction with the compounds which produce the above-described discoloration of the metal surfaces. Nothing is known of the chemical nature of these compounds. If they were only acid-forming components it should be possible to remove them with ammonia, amines or diamines, resulting in a solvent that would produce no discoloration on metal surfaces. Such treatment, however, does not achieve the desired result. The conventional addition of stabilizing agents is not performed until after the treatment in accordance with the invention.

The compounds used in accordance with the invention for the rectification of chlorinated hydrocarbons should be as soluble as possible in water. They all contain an —$NR_2$ group in which R represents an alkyl moiety having a terminal OH group, or an aliphatic or cyclic alkylene moiety, the latter being interrupted by an oxygen bridge in the middle, if desired. R preferably has 1 to 4 carbon atoms in the chain.

The claimed alkanolamines can be characterized by the general formula $[HO-(CH_2)_n-]_m NR_{3-m}$, $n$ being able to assume values between 2 and 4, preferably 2, and $m$ can be equal to 1 or 2 or 3, while R represents an alkyl moiety of one to four carbon atoms, which can be replaced no more than once by hydrogen. Examples of compounds of this group are N-methyl or N-dimethyl ethanolamine, triethanolamine, and N-ethyl-4-aminobutanol-1.

The morpholines are mainly morpholine, N-methylmorpholine or N-ethylmorpholine. The alkyl substituent on the nitrogen atom, however, can also be a higher alkyl moiety of up to 8 carbon atoms.

Hexamethyleneimine, which can also be used, has the formula

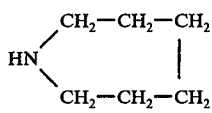

One can also use derivatives of hexamethylene in which the hydrogen atom on the nitrogen atom is replaced by a lower alkyl moiety of up to 8 carbon atoms, such as the methyl or ethyl moiety, for example.

The amount of the compounds to be used in accordance with the invention is not critical. Amounts of as little as 0.1 wt.-% with respect to the chlorinated hydrocarbon will suffice. In general, however, larger amounts will be used, especially when aqueous solutions of the compounds are used. The aqueous solutions are preferably 5 to 50% solutions, depending on the solubility of the compound used. Solvents of higher or lower concentrations, however, can also be used.

The rectification in accordance with the invention can be used with all liquid chlorinated hydrocarbons serving for the cleaning and/or degreasing of metals. It is especially suitable for the chlorination products of 1,2-dichlorethane, such as trichlorethylene and perchlorethylene, for example.

EXAMPLES

The effectiveness of the treatment in accordance with the invention is set forth in the following table representing experiments with perchloroethylene. The claimed compounds (Examples 6 to 10) are compared with compounds of similar structure (ammonia, amines, diamines) and known cleaning agents (phenol).

The experiments were performed as follows: 200 cc of the perchloroethylene being tested was vigorously shaken with 50 cc of an aqueous 10% solution of the compound being tested for effectiveness. After the separation of the two phases, the perchlorethylene was washed neutral with water, dried over silica gel, and then stabilized.

A bright copper strip measuring 10 × 100 mm was then placed in the perchlorethylene such that only half of the metal strip was immersed in the liquid. The specimen was then exposed for one hour to a temperature of 100° C in a drying oven. Then followed the observation or judgment of the copper strip.

| Example | Substance with which perchlorethylene was treated | Judgement of the copper strip |
|---|---|---|
| 1 | Untreated | Gas phase: dark brown<br>Liquid phase: dark brown<br>Phase boundary: plainly apparent |
| 2 | Triethylamine, 10% solution | Gas phase: dark discoloration<br>Liquid phase: dark discoloration<br>Phase boundary: plainly apparent |
| 3 | Ammonia, 10% solution | Gas phase: great discoloration<br>Liquid phase: great discoloration<br>Phase boundary: plainly apparent |
| 4 | Phenol, 10% sol. | Gas phase: dull bluish<br>Liquid phase: slightly dull discoloration<br>Phase boundary: plainly apparent |
| 5 | 1,3-diaminopropane 10% solution | Gas phase: slight discoloration<br>Liquid phase: slight discoloration<br>Phase boundary: mildly discolored |
| 6 | Triethanolamine 10% solution | Gas phase: no discoloration<br>Liquid phase: no discoloration<br>Phase boundary: no discoloration |
| 7 | Morpholine 10% solution | Same as Example 6 |
| 8 | N-diethylethanolamine 10% solution | Same as Example 6 |
| 9 | N-methylmorpholine 10% solution | Same as Example 6 |
| 10 | Hexamethyleneimine 10% solution | Same as Example 6 |

What is claimed is:

1. A method for rectifying chlorinated hydrocarbon to remove therefrom substances which discolor or tarnish metals which comprises contacting said chlorinated hydrocarbon with a compound which is an alkanolamine, morpholine, an N-$C_{1-8}$ alkyl morpholine, hexamethyleneimine, N-$C_{1-8}$ alkyl hexamethyleneimine or a mixture thereof and thereafter water washing the so-contacted chlorinated hydrocarbon.

2. A method according to claim 1 wherein the chlorinated hydrocarbon is contacted with an aqueous solution containing an alkanolamine, morpholine or N-$C_{1-8}$ alkyl hexamethyleneimine.

3. A method according to claim 1 wherein said chlorinated hydrocarbon is contacted with 0.05 to 25 percent by weight of such compound.

4. A method according to claim 1 wherein such chlorinated hydrocarbon is contacted with 0.1 to 10 percent by weight of said compound.

5. A method according to claim 1 wherein said compound is an alkanolamine of the formula $$[HO-(CH_2)n-]_m NR_{3-m}$$

wherein
$n$ is a value of 2 to 4;
$m$ is 1, 2 or 3
R is an alkyl radical of 1 to 4 carbon atoms or hydrogen at least two R moieties being said alkyl radical 6. A method according to claim 1 wherein said compound is morpholine or N-$C_{1-8}$ alkyl morpholine.

7. A method according to claim 1 wherein said compound is morpholine.

8. A method according to claim 1 wherein said compound is N-methyl morpholine or N-ethyl morpholine.

9. A method according to claim 1 wherein said compound is N-methyl or N-dimethyl ethanolamine, triethanolamine or N-ethyl-4-aminobutanol-1.

10. A method according to claim 1 wherein said compound is hexamethyleneimine or N $C_{1-8}$ alkyl hexamethyleneimine.

11. A method according to claim 1 wherein said chlorinated hydrocarbon is trichloroethylene or perchloroethylene and said process is performed prior to stabilization of the chlorinated hydrocarbon.

12. A process according to claim 9 wherein said compound is triethanolamine.

* * * * *